United States Patent [19]
Yamamoto et al.

[11] 4,088,029
[45] May 9, 1978

[54] ULTRASONIC FLAW DETECTOR

[75] Inventors: Eiji Yamamoto, Tokyo; Koji Ohta, Yokohama, both of Japan

[73] Assignee: Kabushikikaisha Tokyo Keiki, Tokyo, Japan

[21] Appl. No.: 668,966

[22] Filed: Mar. 22, 1976

Related U.S. Application Data

[63] Continuation-in-part of Ser. No. 378,804, Jul. 13, 1973, abandoned.

[30] Foreign Application Priority Data

Jul. 14, 1972 Japan .................................. 47-70589

[51] Int. Cl.² ........................................... G01N 29/04
[52] U.S. Cl. ......................................... 73/612; 73/901
[58] Field of Search ............... 73/67.7, 67.8 R, 67.8 S, 73/67.9

[56] References Cited

U.S. PATENT DOCUMENTS

| | | | |
|---|---|---|---|
| 3,041,872 | 7/1962 | Brown et al. | 73/67.9 |
| 3,260,105 | 7/1966 | McNulty | 73/67.9 |
| 3,287,963 | 11/1966 | Stanya et al. | 73/67.9 |
| 3,416,364 | 12/1968 | Wycherley et al. | 73/67.8 S |
| 3,482,435 | 12/1969 | Gunkel | 73/67.9 |
| 3,485,087 | 12/1969 | Brech | 73/67.7 |
| 3,688,565 | 9/1972 | Brech | 73/67.9 |
| 3,805,597 | 4/1974 | Ohta et al. | 73/67.9 |

Primary Examiner—John P. Beauchamp
Attorney, Agent, or Firm—Hill, Gross, Simpson, Van Santen, Steadman, Chiara & Simpson

[57] ABSTRACT

An ultrasonic flaw detector having a probe for transmitting and receiving an ultrasonic wave, a receiver for producing an electric signal in response to the ultrasonic signal from the probe, a plurality of gates and a counter having a corresponding number of independent display elements for indication of detected results. In this case, the detected result can be indicated without using a cathode ray tube.

4 Claims, 21 Drawing Figures

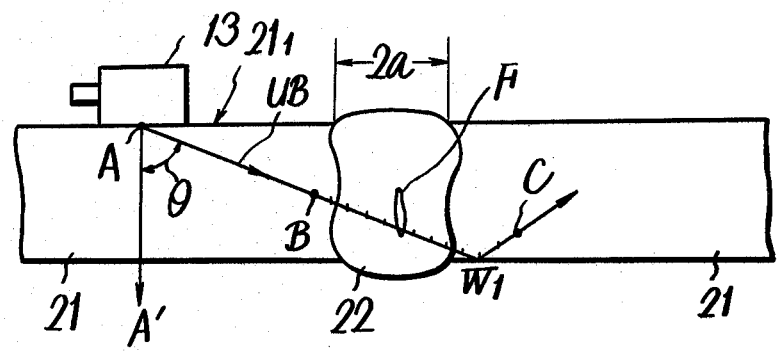
Fig-4
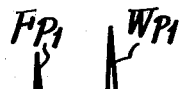
Fig-5A
Fig-5B
Fig-5C
Fig-5D
Fig-5E Fig-8
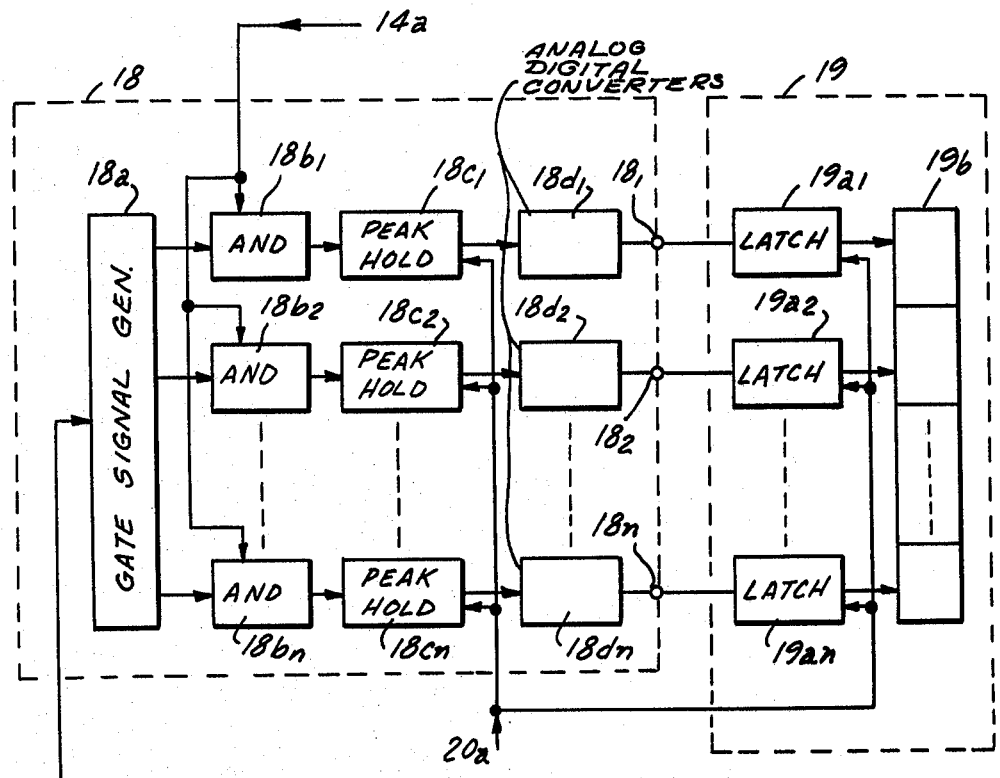
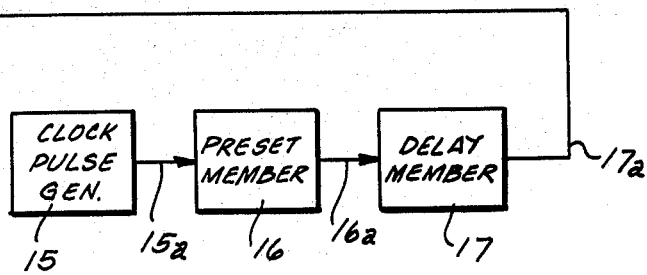

ULTRASONIC FLAW DETECTOR

CROSS REFERENCE TO RELATED APPLICATION

This is a continuation-in-part of our copending application Ser. No. 378,804 filed July 13, 1973, now abandoned.

BACKGROUND OF THE INVENTION

1. Field of the Invention

The present invention relates generally to an ultrasonic flaw detector and more particularly to an ultrasonic flaw detector without using a cathode ray tube.

2. Description of the Prior Art

In a conventional ultrasonic flaw detector, a cathode ray tube is used for achieving ultrasonic flaw detection, so that the entire device becomes bulky and weighty. Further, the conventional ultrasonic flaw detector consumes much electric power and is inconvenient when it is used in the field such as at a dockyard or the like which is inconveniently situated.

In addition, flaw detection with a cathode ray tube requires a skillful operator.

SUMMARY OF THE INVENTION

It is an object of the present invention to provide an ultrasonic flaw detector which is free from the drawbacks encountered in the prior art.

It is another object of the present invention to provide an ultrasonic flaw detector which does not employ a cathode ray tube and is compact and inexpensive.

It is a further object of the prevent invention to provide an ultrasonic flaw detector which is easily operated and indicates the detected result by a numerical display.

Other objects, features and advantages of the invention will become apparent from the following description taken in conjunction with the accompanying drawing.

BRIEF DESCRIPTION OF THE DRAWING

FIG. 4 is a schematic illustrating oblique flaw detection by the ultrasonic flaw detector depicted in FIG. 2;

FIGS. 5A to 5E, inclusive, are waveform diagrams used for explaining flaw detection by the detector shown in FIG. 4;

FIG. 8 is a block diagram used for more detailed explanation of FIG. 2.

DESCRIPTION OF THE PREFERRED EMBODIMENTS

In order to better understand the present invention a conventional ultrasonic flaw detector using a cathode ray tube which achieves a so-called A scope indication will be described with reference to FIGS. 1A and 1B.

Figure 1A:
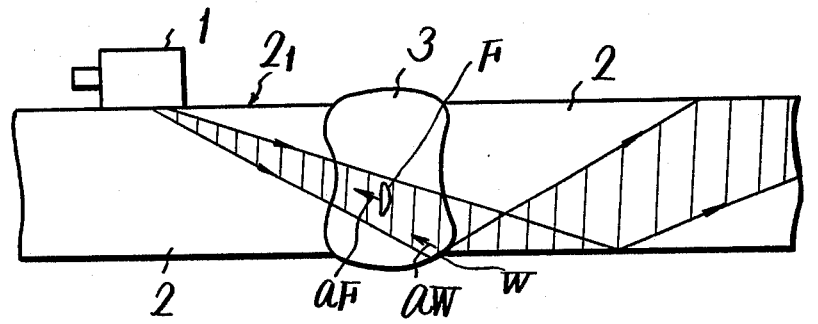
FIGS. 1A and 1B are schematic diagrams showing oblique flaw detection with an ultrasonic flaw detector employing a cathode ray tube.
Figure 1B:
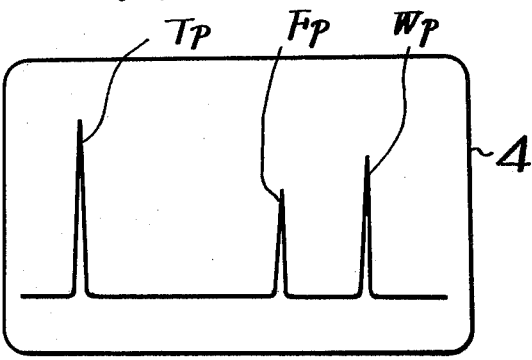

In FIG. 1A, an ultrasonic probe is located on the upper surface $2_1$ of an object such as a steel plate 2 to be detected through a contact medium, for example, oil (not shown). The probe 1 is supplied with a transmitting pulse and scans the surface $2_1$ of the object 2 to achieve so-called oblique ultrasonic flaw detection. An ultrasonic beam is emitted from the probe 1 and transmitted through the inside of the object 2 with some angle as shown in FIG. 1A. If a bead W and a flaw F such as a crack of a welded portion 3 are present in the path of the ultrasonic beam in the object 2, the ultrasonic beam is reflected in the directions shown by arrows $a$W and $a$F, respectively, which reflected echoes are received by the probe 1 which serves as an ultrasonic receiver, also. As a result, pulses $T_P$, $F_P$ and $W_P$ are shown on a screen 4 of the cathode ray tube as in FIG. 1B, where the pulse $T_P$ corresponds to the transmitting pulse, the pulse $W_P$ to the bead echo pulse and the pulse $F_P$ to the flaw echo pulse, respectively. In the prior art, the flaw echo and hence the flaw part or crack F is detected by discriminating the magnitude of the respective echo pulses. As shown in FIG. 1B, the respective pulses $T_P$, $F_P$ and $W_P$ are indicated with suitable time intervals therebetween on the screen 4 of the cathode ray tube.

As mentioned above, according to the prior art, the cathode ray tube is indispensable and hence it is very difficult to reduce the size of the device. If the diameter of the cathode ray tube is reduced, the image of the so-called A scope indication is also reduced and consequently discrimination of the flaw echo becomes difficult.

Thus, it will be easily understood that the prior art ultrasonic flaw detector with the cathode ray tube is very inconvenient for use in the field such as at a dockyard and the like.

An example of the ultrasonic flaw detector according to the present invention which is free from the defects of the prior art will be described below with reference to FIGS. 2 and 3.

Figure 2:
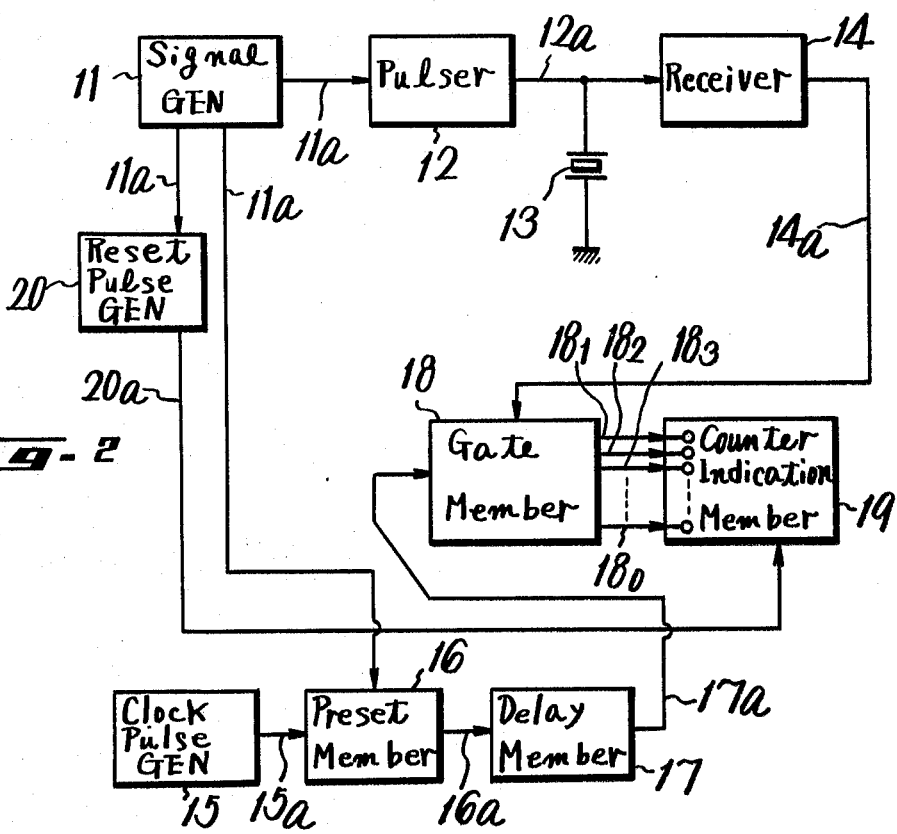
FIG. 2 is a block diagram for showing an example of an ultrasonic flaw detector according to the invention.
Figure 3:
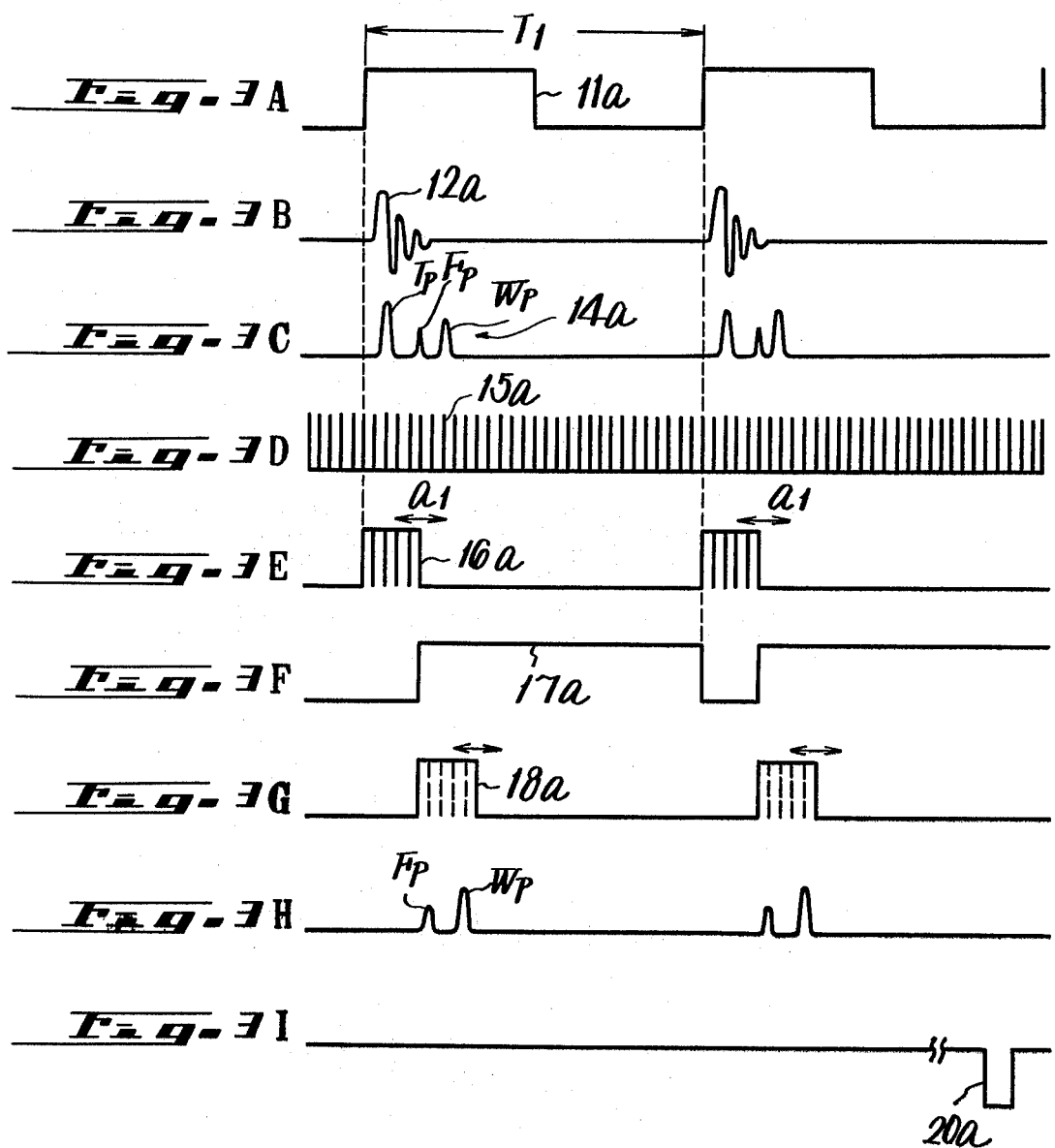
FIGS. 3A to 3I, inclusive, are waveforms used for explaining the operation of the ultrasonic flaw detector shown in FIG. 2.

In FIG. 2, reference numeral 11 designates a synchronizing part or signal generator which produces a rectangular waveform 11$a$, for example, with a predetermined time period $T_1$ (for example, its frequency is about 500~1000 Hz) as shown in FIG. 3A to achieve time control of the ultrasonic flaw detector. The rectangular waveform signal 11$a$ is applied to a pulser 12 which then generates an output pulse signal 12$a$. The pulse signal 12$a$ rises in correspondence with the rising portion of the signal 11$a$ and attenuates abruptly thereafter as shown in FIG. 3B. The pulse signal 12$a$ is fed to a probe 13 which acts as an ultrasonic transmitter and receiver. Thus, the probe 13 emits an ultrasonic wave in response to the pulse signal 12$a$ into an object (not shown) to be detected in the same manner as described in connection with FIG. 1A. The probe 13 is moved across the object in a similar manner to that described in connection with FIG. 1A. A receiver 14 receives echo signals from the probe 13 and then produces output electric signal 14$a$ as shown in FIG. 3C. The electric signal 14$a$ includes a transmitting pulse $T_P$, a flaw echo pulse $F_p$ and a bead echo pulse $W_p$, respectively.

A clockpulse generator 15 such as, for example, a quartz oscillator, which is stable in oscillation frequency, produces a clockpulse 15$a$ as shown in FIG. 3D. A preset member 16 receives the clockpulse 15$a$ from the clockpulse generator 15 and also the rectangular waveform signal 11$a$ from the signal generator 11 and then produces an output pulse 16$a$ as shown in FIG.

3E. That is, the preset member 16 counts the clockpulse 15a by a predetermined number and then produces the pulse 16a. The vertical lines shown within the pulse 16a symbolize the clock pulses. An arrow $a_1$ in FIG. 3E means that the time position of the output pulse 16a from the preset member 16 may be varied by the preset thereof. The output pulse 16a is fed to a delay member 17 which then produces an output signal 17a as shown in FIG. 3F. A gate member 18, which has, for example, ten gate circuits and slicers as shown in FIG. 8, is supplied with the signal 17a and the signal 14a, respectively. The gate member 18 is provided with output terminals $18_1, 18_2, 18_3, \ldots, 18_0$, the number of which corresponds to that of the gate circuits and produces an output signal 18a as shown in FIG. 3G. The vertical lines shown within the pulse 18a symbolize the clock pulses. The output terminals $18_1, 18_2, 18_3, \ldots, 18_0$, are connected to a counter display member 19 at its corresponding input terminals, respectively. The counter display member 19 has independent display elements the number of which correspond to the number of its input terminals, for example, ten, by which the flaw echo $F_P$ and the bead echo $W_P$ are indicated at their magnitude and position, respectively.

FIG. 8 shows a detailed schematic, also in block form, of the blocks 18 and 19 shown in FIG. 2. Delay member 17 is coupled to a gate signal generator 18a and produces a given number, n, of gate pulses which are sequentially shifted as shown in FIG. 3G.

A plurality of AND circuits $18_{b1}, 18_{b2}, \ldots, 18_{bn}$ are coupled to outputs of the gate signal generator and each have an input coupled to the output of the receiver 14; the signal 14a being shown in FIG. 3C.

The output of the AND gates are then coupled to peak hold circuits $18_{c1}, 18_{c2}, \ldots, 18_{cn}$ which hold the peaks of the input signals.

The outputs of the peak hold circuits are coupled to analog-digital converters $18_{d1}, 18_{d2}, \ldots, 18_{dn}$ which convert the peak values received from the peak hold circuits to digital values and deliver them to output terminals $18_1, 18_2, \ldots, 18_n$.

The outputs of the analog-digital converters are then coupled to the display or indication device 19 which includes a plurality of latch circuits $19_{a1}, 19_{a2}, \ldots, 19_{an}$ which in turn are coupled to a display device 19b including (a plurality of) display elements as shown in FIG. 8. The latch circuits latch the signals received from the analog-digital converters and memorize them to supply information to the display which will be held in the display until new information is required to be presented thereon.

The peak hold circuits shown in FIG. 8 also receive a signal 20a which is coupled from the reset generator 20, and this signal is used to reset the system so that another set of data can be supplied to the display unit 19. Also the latch circuits $19_{a(n)}$ are reset by the same signal 20a simultaneously with the resetting of the peak hold circuits.

Also shown in FIG. 8 are the clock pulse generator 15, the preset member 16 and the delay member 17. The clock pulse generator 15 is a quartz crystal oscillator which produces a clock pulse of 16 $MH_z$ which corresponds to the time within which the ultrasonic wave passes through a distance of 1 mm by transverse wave in steel. The preset member 16 may be a preset counter which is preset at a value such that at the end of the preset time or delay time it produces the signal 16a. The delay member 17, is for example, a pulse generator which produces the pulse signal 17a in response to the signal 16a.

By way of example, the velocity of an ultrasonic wave (longitudinal wave) in steel is 5900 m/sec, so that if clockpulses with a frequency of 2.95 $MH_z$ are employed, the wavelength of the ultrasonic wave in the steel is 1 mm. Meantime, the velocity of the ultrasonic wave (transverse wave) at the welded portion of the steel is 3200 m/sec, so that if clockpulses with a frequency of 1.6 $MH_z$ are employed, the wavelength of the ultrasonic wave in the welded portion is 1 mm.

In FIG. 2, the output signal 11a from the signal generator 11 is fed to a reset pulse generator 20 which is provided with a tens counter. The reset pulse generator 20 then produces a pulse signal 20a which corresponds to the drop off portion of the pulse signal 11a as shown in FIG. 3I and which is fed to the counter display device 19 as shown in FIG. 8 to reset the same.

FIG. 4 shows an example where oblique ultrasonic flaw detection is achieved by the ultrasonic flaw detector according to the present invention shown in FIG. 2. As shown in FIG. 4, the probe 13 is placed on one side surface $21_1$ of an object 21 to be detected. If the transmitting pulse 12a is fed to the probe 13, it emits an ultrasonic wave (beam) UB from a point A on the surface $21_1$ to the inside of the object 21 with an angle (refraction angle) $\theta$ with respect to the thickness direction A—A' of the object 21. According to the known document (Ultrasonic flaw detection, A-revised edition (1971) issued by the Japanese Society of non-destructive Inspection), the ultrasonic beam path $W_1$ of one skip is expressed as follows:

$$W_1 = \frac{2t}{\cos\theta}$$

While, the ultrasonic beam path $W_{0.5}$ of 0.5 skip is given as follows:

$$W_{0.5} = \frac{t}{\cos\theta}$$

In the above expressions, $\theta$ represents the refraction angle as mentioned above and $t$ the thickness of the object 21.

In the example of FIG. 4, the ultrasonic beam UB directly emits into the object 21 and the skip number is lower than 0.5. If it is assumed that the width of the bead of a welded portion in the object 21 is taken as $2a$, a time difference $t_D$ (with respect to the starting time B) when the gate is opened is given by the following equation (1).

$$t_D \approx (W_{0.5} - \frac{2a}{\sin\theta}) \frac{2}{V_s} = \quad (1)$$
$$(\frac{t}{\cos\theta} - \frac{2a}{\sin\theta}) \frac{2}{V_s}$$

where $V_s$ represents the velocity of the ultrasonic wave (transverse wave) in the object 21.

The time difference $t_G$ of the distance $\overline{BC}$ where the gate signal generator operate is given by the following equation (2).

$$t_G = (\frac{2a}{\sin\theta}) \frac{2}{V_s} \quad (2)$$

If every gate width is $t'$, the time difference $t_{G'}$ is given as follows:

$$t_{G'} = \left(\frac{a}{5\sin\theta}\right)\frac{2}{V_s} \quad (3)$$

Accordingly, if the refraction angle of the ultrasonic beam from the probe, the bead width of the welded portion and the thickness of the object are known, the time differences $t_D$, $t_G$ and $t_{G'}$ can be calculated easily from the above equations (1) to (3), respectively.

FIG. 5A shows a flaw echo $F_{Pl}$ and a bead echo $W_{Pl}$ corresponding to one bead $W_1$ on the assumption that the delay member 17 is the transmitting time of the ultrasonic wave between the points A and B and the time when the gate is opened corresponds to the time between the points B and C. FIG. 5B shows the condition of the gate member (between the points B and C), that is, shows the conception of OR of the outputs from the gate signal generator 18a, FIG. 5C shows an AND-output of FIGS. 5A and 5B, and FIG. 5D shows an example of the counter display device 19b.

If it is assumed that the thickness of an object to be detected is 30 mm., the refraction angle of the ultrasonic beam from the probe as 70°, the bead width as 14 mm. and the skip number as lower than 0.5 (in the direct emitting used most at present), the time difference $t_D$, $t_G$ and $t_{G'}$ are calculated as follows by the equations (1), (2) and (3):

$t_D = 45.6$ micro-seconds
$t_G = 9.93$ micro-seconds
$t_{G'} = 0.93$ micro-seconds The length is 72.9 mm. between the points A and B and 14.8 mm. between the points B and C. Accordingly, if the delay time is preset to be 45.6 micro-seconds or 73 mm. and the total gate time of the gate member is preset to be 15 mm. or 9.3 micro-seconds, ultrasonic flaw detection can be carried out for the welded portion.

As described above, FIG. 5D shows an example of the display by the counter display member 19 for the detected results, and in FIG. 5D the numeral "0" shows the case where no corresponding echo pulse exists and its position, the numerals other than "0" show the magnitudes and positions of the corresponding echo pulses, respectively. FIG. 5E shows the case where the point "." is used in place of "0" in FIG. 5D and the others are the same as those of FIG. 5D. It is also possible to use the mark "-" in place of "." in FIG. 5E, by way of example.

Figure 6:
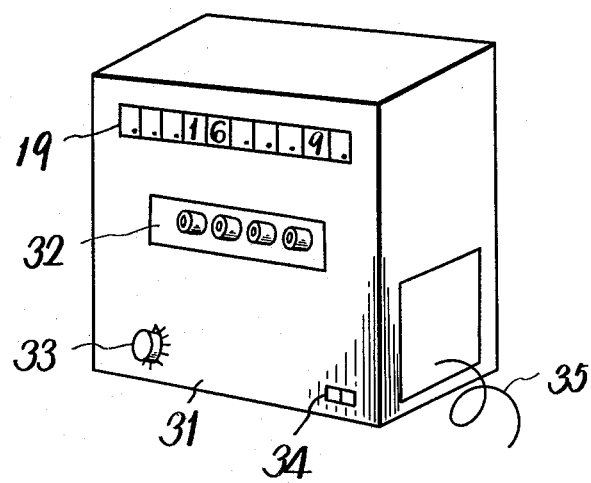
FIG. 6 is a perspective of an external view of the ultrasonic flaw detector of the invention.

FIG. 6 shows the ultrasonic flaw detector according to the present invention as a whole. On the front panel 31 thereof, there are arranged the counter indication member 19, a knob assembly 32 for presetting the preset member 16, and the gate member 18, a knob 33 for adjusting the sensitivity of the receiver 14 and a power source switch 34, respectively. In FIG. 6, reference numeral 35 shows a lead wire connected to the probe 13.

In practical flaw detection, it is important to detect the position of the flaw and its depth from the surface of the object. The ultrasonic flaw detector of the invention described above, however, does not indicate the depth of the flaw from the surface of the object directly, but it may be possible to assume the depth of the flaw based upon the distance of the preset member and the number of the gate where the flaw echo appears.

If the depth of the flaw from the surface of the object to be detected is taken as $d$ in the case of direct emitting flaw detection, the depth $d$ is given as follows:

$$d = (\overline{AB} + \overline{BF})\cos\theta$$

which will be apparent from FIG. 4.

If the flaw echo with a height (magnitude) of 6 appears in the sixth gate as shown in FIGS. 5D and 5E, the depth $d_6$ of the flaw from the surface of the object is given as follows:

$$d_6 = (72.9 + 14.8 \times 0.6)\cos 70° \text{ mm.} \doteq 27 \text{ mm.}$$

Accordingly, if the various echoes are assumed, their depths are calculated and the calculated results are shown as a table, the depth of the flaw can be easily obtained by the table. It is, of course, easily possible to calculate the depth of flaws by an electronic calculator without employing the table.

Figure 7:
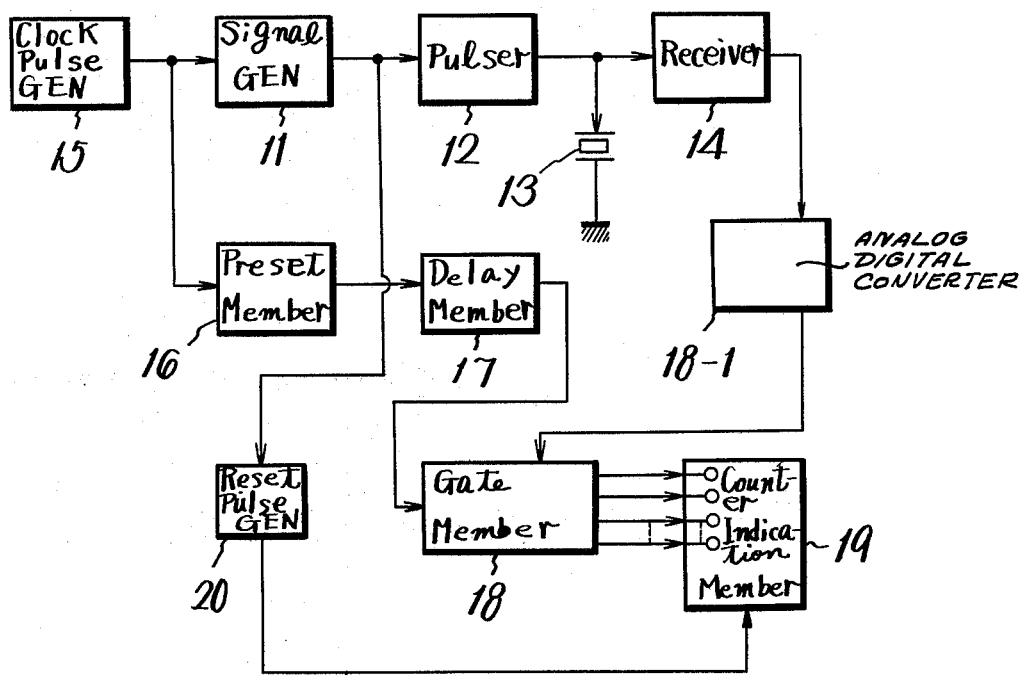
FIG. 7 is a block diagram showing another example of the invention.

FIG. 7 is a block diagram for showing another example of the present invention. In FIG. 7, the output from the clockpulse generator 15 is counted down by the signal generator 11 and then supplied to the pulser 12, while a single slicer 18-1 is provided between the receiver 14 and the gate member 18 instead of those provided in the gate member 18 in the example of FIG. 2. The other circuit construction of FIG. 7 is substantially the same as that of FIG. 2.

It will be apparent that ultrasonic flaw detection can be performed by the example of FIG. 7 in the same manner as that of FIG. 2.

It must be noted that there exists a time delay between the vibrator or transmitter of the probe and a wedge, which time delay may be also referred to as a delay between the transmitting signal and the incidence point. In practice, the time delay is about 7 microseconds for a wedge with an effective width of 10 mm., but, in general, the time delay is constant for a probe. Accordingly, the preset is done in consideration of the above time delay.

The foregoing description is given for the case where the ultrasonic flaw detector according to the invention is used for achieving the oblique flaw detection. It will be apparent that the ultrasonic flaw detector of the invention can be used for vertical flaw detection, similarly.

Further, it will be apparent that the preset member is not limited to the use of a preset counter 16 but can use one shot multivibrator or the Miller integrator.

As described above, with the present invention the result of the ultrasonic flaw detection can be directly viewed without using a cathode ray tube, so that the ultrasonic flaw detector of the present invention is effective in practical use and free from the drawbacks inherent in the prior art.

It will be apparent that many modifications and variations can be effected without departing from the spirit and scope of the novel concepts of the present invention.

We claim:
1. An ultrasonic flaw detector comprising:
   (a) means including a signal generator for applying a transmitting pulse to a probe, said probe transmitting an ultrasonic wave to an object having a flaw to be detected;
   (b) receiver means for receiving a reflected ultrasonic wave arriving at said probe from a flaw in the object being detected due to reflection of said transmitting ultrasonic wave from said flaw;

(c) gate circuit means including a gate signal generator which produces plural output signals, said plural output signals occurring without a gap from a preceding one of said signals, AND circuits, peak hold circuits and analog-digital converters, each of said AND circuits receiving the output signal from said gate signal generator sequentially, and an output signal from each of said AND circuits being supplied through each of said peak hold circuits to each of said analog-digital converters;

(d) means for coupling an output from said receiver means to said gate circuit means;

(e) clock pulse generating means for producing a clock pulse;

(f) preset means for receiving the clock pulse from said clock pulse generating means and said transmitting pulse from said signal generator and producing an output signal for a fixed count of clock pulses from said clock pulse generating means;

(g) delay circuit means coupled to an output of said preset means and producing a single output signal for each cycle of said signal generator, said single output signal being applied to said gate circuit means, said plural output signals from said gate signal generator being produced in response to said single output signal from said delay circuit means; and (h) counter indication means including latch circuits and display elements, each of said display elements receiving an output signal from each of said analog-digital converters through each of said latch circuits to give quantitative data concerning a flaw magnitude in said object being detected in response to measurements of said reflected ultrasonic wave.

2. An ultrasonic flaw detector as claimed in claim 1 in which said gate circuit means includes a plurality of gate circuits and the same number of analog to digital converters and said counter indication means includes a plurality of independent indication elements, the output from each of said analog to digital converters being applied to a corresponding indication element to numerically indicate the magnitude and position of the detected flaw.

3. An ultrasonic flaw detector as claimed in claim 1 in which a common analog to digital converter is inserted between said receiver and said gate circuit means.

4. An ultrasonic flaw detector as claimed in claim 1 in which the signal generator is coupled to said preset member for controlling the same, reset means coupled to the counter indication means, said signal generator being also coupled to said reset means for time-controlling the counter indication means.

* * * * *